(12) United States Patent
Lagrange

(10) Patent No.: US 7,326,258 B2
(45) Date of Patent: Feb. 5, 2008

(54) COMPOSITIONS COMPRISING HYDROXYALKYL DIRECT DYES, IMPLEMENTATION PROCESSES AND USES THEREOF

(75) Inventor: Alain Lagrange, Coupvray (FR)

(73) Assignee: L'Oreal S.A., Paris (FR)

( * ) Notice: Subject to any disclaimer, the term of this patent is extended or adjusted under 35 U.S.C. 154(b) by 283 days.

(21) Appl. No.: 11/155,501

(22) Filed: Jun. 20, 2005

(65) Prior Publication Data

US 2005/0278872 A1 Dec. 22, 2005

Related U.S. Application Data

(60) Provisional application No. 60/616,433, filed on Oct. 7, 2004.

(51) Int. Cl.
A61K 7/13 (2006.01)
(52) U.S. Cl. ............ 8/405; 8/406; 8/409; 8/411; 8/412; 8/435; 548/150; 544/99
(58) Field of Classification Search ........... 8/405, 8/406, 408, 409, 411, 412, 435; 548/150; 544/99
See application file for complete search history.

(56) References Cited

U.S. PATENT DOCUMENTS

| 4,003,699 A | 1/1977 | Rose et al. |
|---|---|---|
| 4,072,911 A | 2/1978 | Walther et al. |
| 4,823,985 A | 4/1989 | Grollier et al. |
| 5,061,289 A | 10/1991 | Clausen et al. |
| 5,220,009 A | 6/1993 | Mazur et al. |
| 5,380,340 A | 1/1995 | Neunhoeffer et al. |
| 5,534,267 A | 7/1996 | Neunhoeffer et al. |
| 5,663,366 A | 9/1997 | Neunhoeffer et al. |
| 5,708,151 A | 1/1998 | Mockli |
| 5,766,576 A | 6/1998 | Lowe et al. |
| 6,001,134 A * | 12/1999 | S.o slashed.rensen .......... 8/401 |
| 6,099,592 A | 8/2000 | Vidal et al. |
| 6,284,003 B1 | 9/2001 | Rose et al. |
| 6,338,741 B1 | 1/2002 | Vidal et al. |
| 6,645,258 B2 | 11/2003 | Vidal et al. |
| 6,730,789 B1 | 5/2004 | Birault et al. |
| 2004/0029837 A1 | 2/2004 | Fries et al. |

FOREIGN PATENT DOCUMENTS

| DE | 23 59 399 | 6/1975 |
|---|---|---|
| DE | 38 43 892 | 6/1990 |
| DE | 41 33 957 | 4/1993 |
| DE | 195 43 988 | 5/1997 |
| EP | 0 339 889 | 11/1989 |
| EP | 0 527 648 | 2/1993 |
| EP | 0 714 954 | 6/1996 |
| EP | 0 770 375 | 5/1997 |
| EP | 1 491 590 | 12/2004 |
| FR | 2 586 913 | 3/1987 |
| FR | 2 733 749 | 11/1996 |
| FR | 2 801 308 | 5/2001 |
| GB | 1026978 | 4/1966 |
| GB | 1153196 | 5/1969 |
| GB | 1503380 | 3/1978 |
| GB | 1586820 | 3/1981 |
| JP | 2-19576 | 7/1988 |
| JP | 5-163124 | 6/1993 |
| JP | 9-241558 | 9/1997 |
| JP | 11-58977 | 3/1999 |
| WO | WO 94/08969 | 4/1994 |
| WO | WO 94/08970 | 4/1994 |
| WO | WO 95/01772 | 1/1995 |
| WO | WO 95/15144 | 6/1995 |
| WO | WO 96/15765 | 5/1996 |
| WO | WO 97/19998 | 6/1997 |
| WO | WO 97/19999 | 6/1997 |
| WO | WO 97/37633 | 10/1997 |
| WO | WO 02/20670 | 3/2002 |

(Continued)

OTHER PUBLICATIONS

STIC Search Report dated May 14, 2007.*

(Continued)

*Primary Examiner*—Eisa Elhilo
(74) *Attorney, Agent, or Firm*—Finnegan, Henderson, Farabow, Garrett & Dunner L.L.P.

(57) ABSTRACT

The present invention relates to a cosmetic composition for dyeing keratin fibres, in particular human keratin fibres such as the hair, comprising, in a suitable dyeing medium, at least one hydroxyalkyl compound of general formula (I) below:

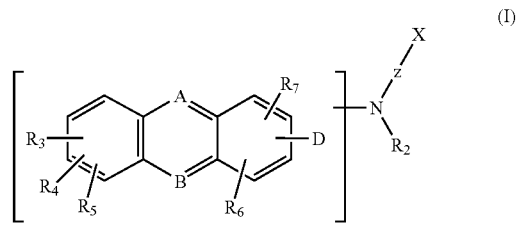

and at least one cosmetic adjuvant according to the invention.

The present invention also relates to a process for dyeing keratin fibres using these compositions based on hydroxyalkyl compounds, to a device with compartments and to the use of these compounds in hair dyeing.

24 Claims, No Drawings

FOREIGN PATENT DOCUMENTS

| WO | WO 02/096896 | 12/2002 |
|---|---|---|
| WO | WO 03/080736 | 10/2003 |

OTHER PUBLICATIONS

Brown, et al., "The role of the primary intermediate, N,N-bis(20hydroxyethyl)-p-phenylenediamine in oxidate hair dyeing," *J. Soc. Cosm. Chem.* 37(1): 1-8 (1986).

Chemical Abstract XP-002316192 for Brown, et al., "The role of the primary intermediate, N,N-bis(2-hydroxyethyl)-p-phenylenediamine in oxidative hair dyeing," *J. Soc. Cosm. Chem.* 37(1): 1-8 (1986).

Chemical Abstract XP-002316193 for WO 97/37633 (1997).
Chemical Abstract XP-002316194 for WO 97/19999 (1997).
Chemical Abstract XP-002316195 for WO 97/19998 (1997).
Chemical Abstract XP-002343905 for Sebe et al., "Basic Oxazine Dyes," *Revistade Chimie* (Bucharest, Romania) 41(5-6):426-8 (1990).

Chemical Abstract XP-002343906 for Burton, "Ground and exdited state chemistry of some hydrophilic thiazine dyes for possible photogalvanic applications," Energy Res. Abstr., 9(10), Abstr. No. 18344 (1984).

English Language DERWENT Abstract for EP 0 770 375 (1997).
English Language DERWENT Abstract for JP 2-19576 (1988).
English Language DERWENT Abstract for JP 5-163124 (1993).
Patent Abstract of Japan for JP 9-241558 (1997).
Patent Abstract of Japan for JP 11-58977 (1999).
International Search Report mailed Feb. 3, 2005 in FR 0406675 (corresponding to the present application).

* cited by examiner

COMPOSITIONS COMPRISING HYDROXYALKYL DIRECT DYES, IMPLEMENTATION PROCESSES AND USES THEREOF

This application claims benefit of U.S. Provisional Application No. 60/616,433, filed Oct. 7, 2004, the contents of which are incorporated herein by reference. This application also claims benefit of priority under 35 U.S.C. § 119 to French Patent Application No. 04 06675, filed Jun. 18, 2004, the contents of which are also incorporated by reference.

The present patent application relates to cosmetic compositions comprising hydroxyalkyl compounds for the direct dyeing of keratin fibres, in particular human keratin fibres such as the hair, to processes using this composition, to a multi-compartment device and to the use of the hydroxyalkyl compounds.

It is known practice to dye keratin fibres, and in particular human hair, with dye compositions containing oxidation dye precursors, which are generally known as oxidation bases, such as ortho- or para-phenylenediamines, ortho- or para-aminophenols, and heterocyclic compounds. These oxidation bases are colourless or weakly coloured compounds that, when combined with oxidizing products, may give rise to coloured compounds by a process of oxidative condensation.

It is also known that the shades obtained with these oxidation bases may be varied by combining them with couplers or coloration modifiers, the latter being chosen especially from aromatic meta-diamines, meta-aminophenols, meta-diphenols and certain heterocyclic compounds such as indole compounds.

The variety of molecules used as oxidation bases and couplers allows a wide range of colours to be obtained.

The "permanent" coloration obtained using these oxidation dyes must moreover satisfy a certain number of requirements. Thus, it must have no toxicological drawback, it must be able to produce shades in the desired intensity, and it must show good resistance to external agents such as light, bad weather, washing; permanent-waving, perspiration and rubbing.

The dyes must also be able to cover grey hair and, finally, they must be as unselective as possible, i.e. they must produce the smallest possible differences in coloration along the same keratin fibre, which is generally differently sensitized (i.e. damaged) between its end and its root.

It is also known practice to dye keratin fibres by direct or semi-permanent dyeing. The process conventionally used in direct dyeing consists in applying to the keratin fibres direct dyes, which are coloured and colouring molecules with affinity for the fibres, leaving the coloured molecules on the fibres to allow them to penetrate, by diffusion, into the hair, and then rinsing the fibres.

It is known practice, for example, to use nitrobenzene, anthraquinone, nitropyridine, azo, xanthene, acridine, azine or triarylmethane direct dyes.

This results in colorations that may be particularly chromatic, but which are, however, temporary or semi-permanent on account of the nature of the bonds between the direct dyes and the keratin fibre. These interactions are such that desorption of the dyes from the surface and/or the core of the fibre takes place easily. The colorations generally show low dyeing power and poor fastness with respect to washing or perspiration.

In contrast with oxidation dye compositions, direct or semi-permanent dye compositions are generally used without the presence of an oxidizing agent. These colorations may be performed repeatedly without degrading the keratin fibre.

There is a real need for direct dye compositions that are improved in terms of harmlessness, fastness and selectivity.

The Applicant has just discovered, surprisingly and advantageously, a novel family of hydroxyalkyl compounds used as direct dyes for the preparation of compositions for dyeing keratin fibres, in particular human keratin fibres such as the hair, which allow these improvements.

Besides their advantage in terms of harmlessness, the hydroxyalkyl direct dyes according to the present patent application give colorations that are resistant to external agents (sunlight and bad weather) and also to shampooing and perspiration.

In addition, the compositions comprising these hydroxyalkyl direct dyes have a good toxicological profile.

A first subject of the present invention consists of a cosmetic composition for dyeing keratin fibres, in particular human keratin fibres such as the hair, comprising, in a suitable dyeing medium, at least one particular hydroxyalkyl direct dye and at least one cosmetic adjuvant.

A second subject of the present patent application consists of a process for dyeing keratin fibres, in particular human keratin fibres such as the hair, using these compositions based on hydroxyalkyl direct dyes.

Another subject of the present patent application relates to a multi-compartment device comprising the composition according to the invention.

Another subject of the present patent application consists of the use of hydroxyalkyl direct dyes according to the present invention for dyeing keratin fibres, in particular human keratin fibres such as the hair.

Other characteristics, aspects, objects and advantages of the present invention will emerge even more clearly on reading the description and the examples that follow.

The invention relates to a cosmetic composition for dyeing keratin fibres, in particular human keratin fibres such as the hair, comprising, in a suitable dyeing medium:

at least one hydroxyalkyl compound of formula (I) below:

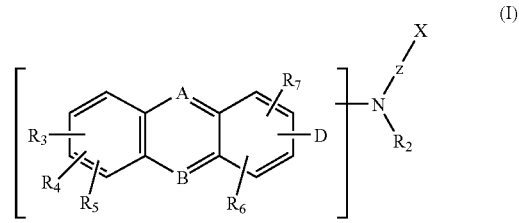

in which:

A represents a nitrogen atom or a group $NR_9$ or $CR_9$;

B represents an oxygen, sulfur or nitrogen atom or a group $—CR_9$;

A and B representing at least one hetero atom bearing a permanent cationic charge;

the electrical neutrality of the compound of formula (I) is ensured by an external counterion Y and/or by one of the substituents borne by the tricyclic nucleus;

D represents an amino group, which is unsubstituted or mono- or disubstituted with one or more linear or branched $C_1$-$C_{24}$ alkyl groups, which may be interrupted with one or more hetero atoms and/or which may be substituted, the substituent(s) on the amino group together possibly forming a 5- to 12-membered optionally aromatic saturated or unsaturated heterocycle, these substituents themselves possibly being substituted with a sulfonic acid and/or a carboxylic acid; an amino group which is mono- or disubstituted with an optionally substituted aryl group, D being in the position para to the carbon that bears A or in the position para to the carbon that bears B;

the substituent —N(zX)R$_2$ is borne by the tricyclic nucleus;

z represents a linear or branched C$_1$-C$_{24}$ alkylene radical optionally interrupted with one or more hetero atoms, preferably oxygen, bearing a substituent X of

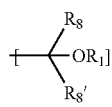

formula (II) below:

R$_1$ represents a hydrogen atom or a C$_1$-C$_{24}$ hydroxyalkyl group;

R$_8$ and R$_8$' represent, independently of each other, a hydrogen atom or a C$_1$-C$_{24}$ alkyl group which may be interrupted with one or more hetero atoms or a carbonyl group and/or which may be substituted;

R$_2$ represents a hydrogen atom; a linear or branched C$_1$-C$_{24}$ alkyl radical, which may be interrupted with one or more hetero atoms or a carbonyl group and/or which may be substituted; or a hydroxyalkyl group;

R$_3$, R$_4$, R$_5$, R$_6$ and R$_7$ represent, independently of each other, a hydrogen or halogen atom; a linear or branched C$_1$-C$_{24}$ alkyl radical, which may be interrupted with one or more hetero atoms or a carbonyl group and/or which may be substituted; an amino group, which is unsubstituted or mono- or disubstituted with one or more linear or branched C$_1$-C$_{24}$ alkyl groups, which may be interrupted with one or more hetero atoms or carbonyl groups and/or which may be substituted, the substituent(s) on the amino group together possibly forming a 5- to 12-membered optionally aromatic saturated or unsaturated heterocycle; optionally substituted with a carboxylic acid and/or a sulfonic acid;

when R$_2$ represents a hydrogen atom, then D, R$_3$, R$_4$, R$_5$, R$_6$ or R$_7$ represents a disubstituted amino group;

R$_9$ represents a linear or branched, substituted or unsubstituted C$_1$-C$_{24}$ alkyl group, a benzyl or aryl radical optionally substituted with at least one C$_1$-C$_{24}$ alkyl group, at least one C$_1$-C$_{24}$ alkoxy group, at least one carboxylic acid and/or at least one sulfonic acid group;

and the mesomeric forms thereof; and at least one cosmetic adjuvant.

Preferably, the composition comprises the hydroxyalkyl compound of formula (III):

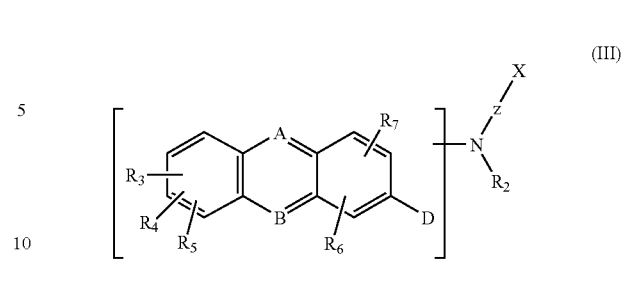

in which:

A, B, D, —N(zX)R$_2$, R$_1$, R$_8$ and R$_8$', R$_2$, R$_3$, R$_4$, R$_5$, R$_6$, R$_7$ and R$_9$ have the same meaning as in the compound of formula (I) defined above.

Preferably, the composition comprises the compound of formula (V):

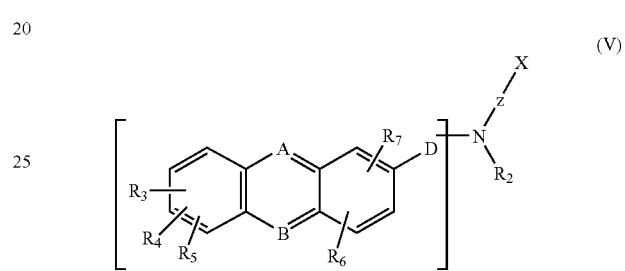

in which:

A, B, D, —N(zX)R$_2$, R$_1$, R$_8$ and R$_8$', R$_2$, R$_3$, R$_4$, R$_5$, R$_6$, R$_7$ and R$_9$ have the same meaning as in the compound of formula (I) defined above.

The term "substituted" means substituted with a linear or branched C$_1$-C$_6$ alkyl group; a linear or branched C$_1$-C$_6$ hydroxyalkyl group; an acetylamino group; a hydroxyl group; a cyano group; a halogen atom; preferably fluorine and brome, a linear or branched C$_1$-C$_6$ alkoxy group; a linear or branched C$_1$-C$_6$ alkylcarbonyl group; a hydroxycarbonyl group; a linear or branched C$_1$-C$_6$ alkoxycarbonyl group; an aryl group substituted with one of the abovementioned substituents.

Preferably, R$_3$, R$_4$, R$_5$, R$_6$ and R$_7$ represent a hydrogen atom.

According to one particular embodiment, the substituents D and N(zX)R$_2$ are on different aromatic rings.

According to one preferable embodiment, the substituent N(zX)R$_2$ is in the position para to the carbon that bears A or in the position para to the carbon that bears B.

Preferably, the compounds of formula (I) according to the present invention are:

| STRUCTURE | NAME |
|---|---|
| 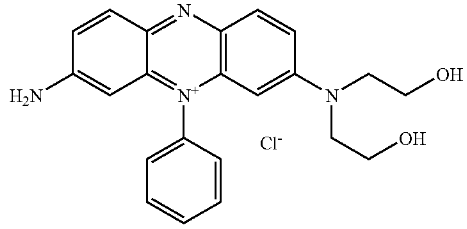 | 3-Amino-7-[bis(2-hydroxyethyl)amino]-5-phenyl phenazinium chloride, |

-continued

| STRUCTURE | NAME |
|---|---|
| | 3-[Bis(2-hydroxyethyl)amino]-7-(dimethylamino)-5-(4-methoxyphenyl)phenazinium iodide |
| 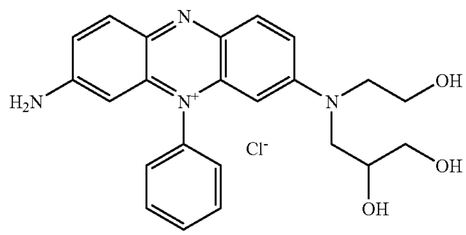 | 3-Amino-7-[(2,3-dihydroxypropyl)(2-hydroxyethyl)amino]-5-phenylphenazinium chloride |
| | 3-Amino-7-[(2-hydroxyethyl)methylamino]-5-phenylphenazinium chloride |
| 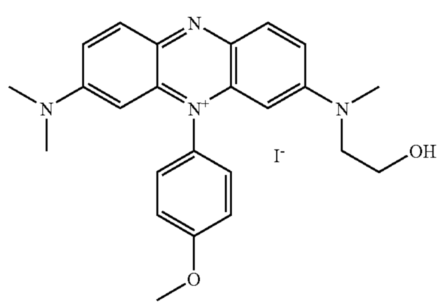 | 3-(Dimethylamino)-7-[(2-hydroxyethyl)methylamino]-5-(4-methoxyphenyl)phenazinium iodide |
| 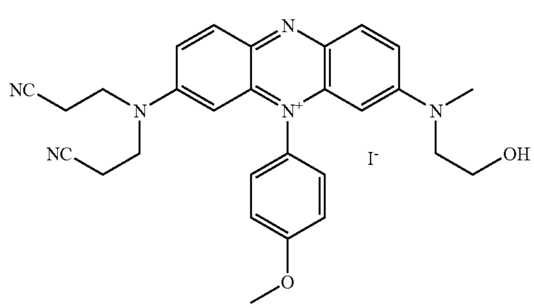 | 3-[Bis(2-cyanoethyl)amino]-7-[(2-hydroxyethyl)methylamino]-5-(4-methoxyphenyl)phenazinium iodide |

-continued

| STRUCTURE | NAME |
|---|---|
| 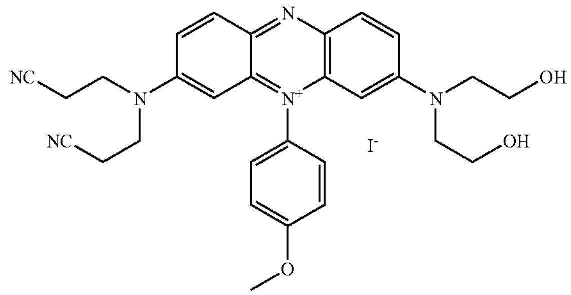 | 3-[Bis(2-cyanoethyl)amino]-7-[bis(2-hydroxyethyl)amino]-5-(4-methoxyphenyl)phenazinium iodide |
| 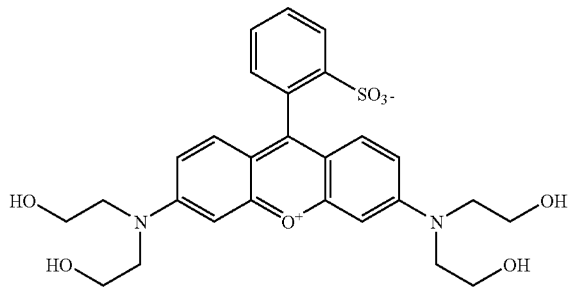 | Internal salt of 3,6-bis[bis(2-hydroxyethyl)amino]-9-(2-sulfophenyl)xanthylium |
| 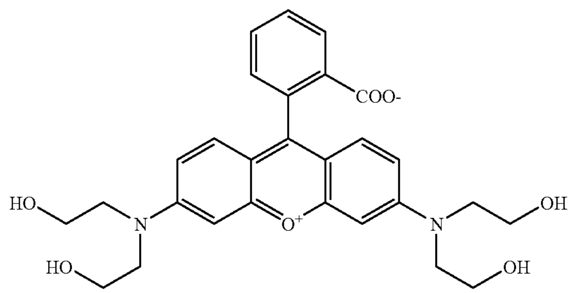 | Internal salt of 3,6-bis[bis(2-hydroxyethyl)amino]-9-(2-carboxyphenyl)xanthylium |
| 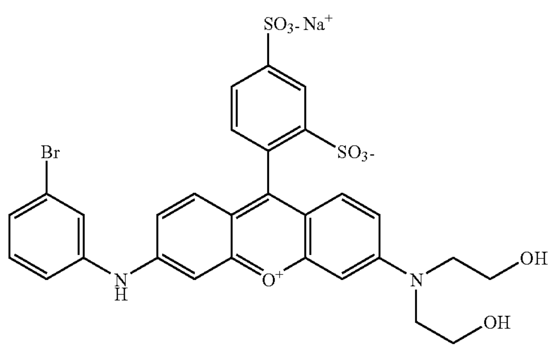 | Sodium salt of 3-[bis(2-hydroxyethyl)amino]-6-[(2-bromophenyl)amino]-9-(2,4-disulfophenyl)xanthylium |
|  | Sodium salt of 3-[bis(2-hydroxyethyl)amino]-9-(2,4-disulfophenyl)-6-[(2-fluorophenyl)amino]xanthylium |

-continued

| STRUCTURE | NAME |
|---|---|
| 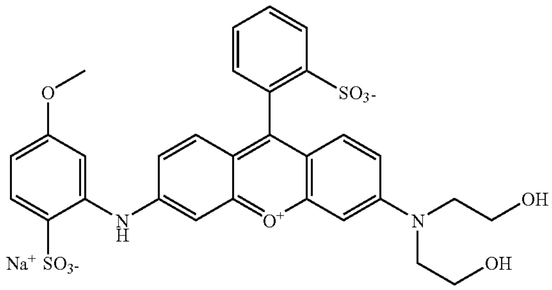 | Sodium salt of 3-[bis(2-hydroxyethyl)amino]-6-[(2-methoxy-5-sulfophenyl)amino]-9-(2-sulfophenyl)xanthylium |
| | Sodium salt of 3-[bis(2-hydroxyethyl)amino]-9-(2,4-disulfophenyl)-6-[[2-(1-methylethoxy)-phenyl]amino]xanthylium |
| 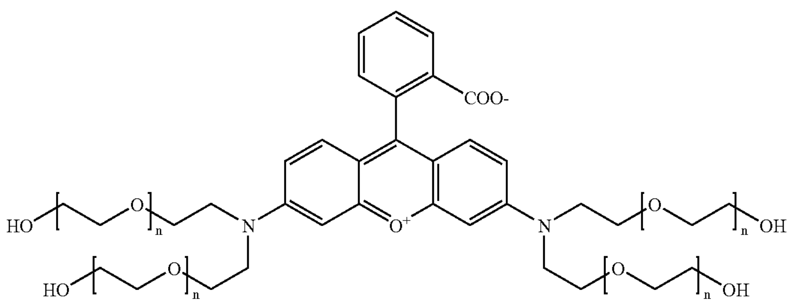 | Poly(oxy-1,2-ethanediyl), α-hydro-ω-hydroxy ether with internal salt of 3,6-[bis(2-hydroxyethyl)amino]-9-(2-carboxyphenyl)xanthylium |
| 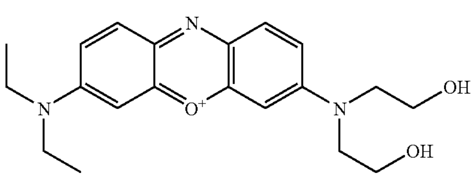 | 3-[Bis(2-hydroxyethyl)amino]-7-(diethylamino)phenoxazin-5-ium |
| 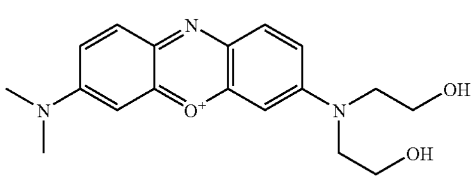 | 3-[Bis(2-hydroxyethyl)amino]-7-(dimethylamino)phenoxazin-5-ium, |
| 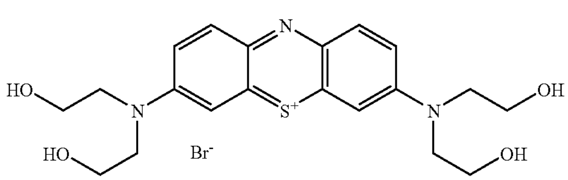 | 3,7-Bis(bis(2-hydroxyethyl)-amino)phenothiazin-5-ium bromide |

The term "mesomer" means a compound in which the double bonds can delocalize by resonance. Examples of mesomeric forms of some of the preferred compounds are outlined below.

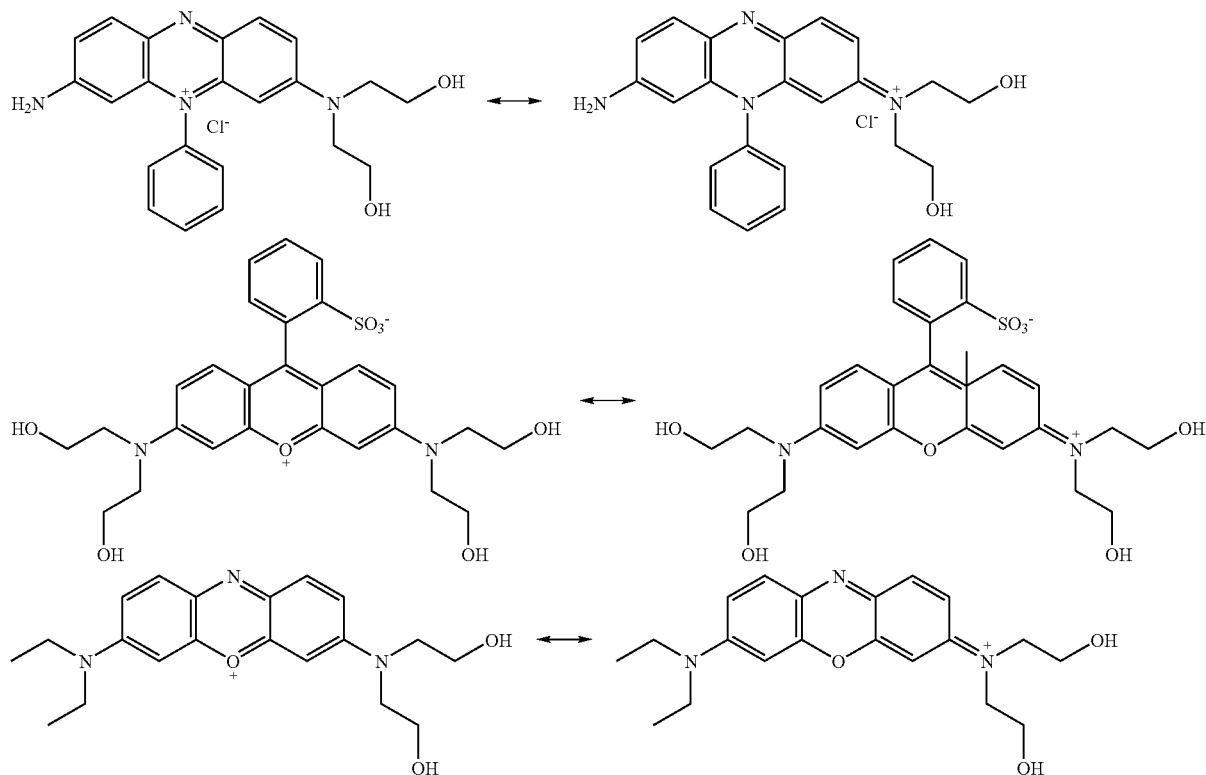

The compound of formula (I) bears at least one permanent cationic charge on a hetero atom of the group A or B. This charge is due to a coordination bond number higher than the valency number of the hetero atom. As a result, it is independent of the pH of the medium.

This cationic charge may be neutralized with a counterion present within the same compound, for instance a sulfonate or a carboxylate borne by the substituents of the tricyclic nucleus or by $R_9$.

When this cationic charge is not neutralized with an internal counterion, the electrical neutrality of the compound of formula (I) is ensured by a counterion Y that is external to the said compound.

Y is an anionic counterion chosen from an iodide, a bromide, a chloride, an ethyl sulfate and a methyl sulfate.

When the compound of formula (I) bears a negative charge number higher than the cationic charge number, then the counterion Y is cationic.

Y is a cationic counterion chosen from sodium and potassium.

Preferably, the compound of formula (I) bears only one permanent cationic charge on a hetero atom of the group A or B.

The composition based on these hydroxyalkyl direct dyes of formula (I) according to the present invention comprises from 0.001% to 20%, preferably from 0.01% to 10% and preferentially from 0.1% to 5% by weight of direct dye(s) of formula (I) relative to the total weight of the composition.

The cosmetic adjuvant(s) contained in the composition according to the invention is (are) chosen from surfactants, polymers, ceramides and pseudoceramides, vitamins and provitamins, sunscreens, solid compounds such as pigments, nacreous agents or opacifiers, direct dyes other than those of formula (I), oxidation dye precursors, sequestering agents, plasticizers, solubilizers, acidifying agents, basifying agents, neutralizers, mineral and organic thickeners, antioxidants, hydroxy acids, solvents, penetrating agents, buffers, dispersants, conditioning agents and preserving agents.

The above adjuvants are generally present in an amount for each of between 0.01% and 20% by weight relative to the total weight of the composition.

Needless to say, a person skilled in the art will take care to select this or these compound(s) such that the advantageous properties intrinsically associated with the direct dye composition in accordance with the invention are not, or are not substantially, adversely affected by the envisaged addition(s).

The additional direct dye(s) according to the invention is (are) chosen from neutral, acidic or cationic nitrobenzene dyes, neutral, acidic or cationic azo direct dyes, neutral, acidic or cationic quinone and in particular anthraquinone direct dyes, azine direct dyes, triarylmethane direct dyes, indoamine direct dyes and natural direct dyes.

Among the benzene-based direct dyes that may be used according to the invention, mention may be made, in a non-limiting manner, of the following compounds:

1,4-diamino-2-nitrobenzene
1-amino-2-nitro-4-(β-hydroxyethylamino)benzene
1-amino-2-nitro-4-bis(β-hydroxyethyl)aminobenzene
1,4-bis(β-hydroxyethylamino)-2-nitrobenzene 1-β-hydroxyethylamino-2-nitro-4-bis(β-hydroxyethylamino)benzene
1-β-hydroxyethylamino-2-nitro-4-aminobenzene
1-β-hydroxyethylamino-2-nitro-4-(ethyl) (β-hydroxyethyl)aminobenzene
1-amino-3-methyl-4-β-hydroxyethylamino-6-nitrobenzene
1-amino-2-nitro-4-β-hydroxyethylamino-5-chlorobenzene
1,2-diamino-4-nitrobenzene
1-amino-2-β-hydroxyethylamino-5-nitrobenzene
1,2-bis(β-hydroxyethylamino)-4-nitrobenzene
1-amino-2-[tris(hydroxymethyl)methylamino]-5-nitrobenzene
1-hydroxy-2-amino-5-nitrobenzene
1-hydroxy-2-amino-4-nitrobenzene
1-hydroxy-3-nitro-4-aminobenzene
1-hydroxy-2-amino-4,6-dinitrobenzene
1-β-hydroxyethyloxy-2-β-hydroxyethylamino-5-nitrobenzene
1-methoxy-2-β-hydroxyethylamino-5-nitrobenzene
1-β-hydroxyethyloxy-3-methylamino-4-nitrobenzene
1-β,γ-dihydroxypropyloxy-3-methylamino-4-nitrobenzene
1-β-hydroxyethylamino-4-β,γ-dihydroxypropyloxy-2-nitrobenzene
1-β,γ-dihydroxypropylamino-4-trifluoromethyl-2-nitrobenzene
1-β-hydroxyethylamino-4-trifluoromethyl-2-nitrobenzene
1-β-hydroxyethylamino-3-methyl-2-nitrobenzene
1-β-aminoethylamino-5-methoxy-2-nitrobenzene
1-hydroxy-2-chloro-6-ethylamino-4-nitrobenzene
1-hydroxy-2-chloro-6-amino-4-nitrobenzene
1-hydroxy-6-[bis(β-hydroxyethyl)amino]-3-nitrobenzene
1-β-hydroxyethylamino-2-nitrobenzene
1-hydroxy-4-β-hydroxyethylamino-3-nitrobenzene.

Among the azo direct dyes that may be used according to the invention, mention may be made of the cationic azo dyes described in patent applications WO 95/15144, WO 95/01772 and EP 714 954, the content of which forms an integral part of the invention.

Among these compounds, mention may be made most particularly of the following dyes:
  1,3-dimethyl-2-[[4-(dimethylamino)phenyl]azo]-1H-imidazolium chloride,
  1,3-dimethyl-2-[(4-aminophenyl)azo]-1H-imidazolium chloride,
  1-methyl-4-[(methylphenylhydrazono)methyl]pyridinium methyl sulfate.

Among the azo direct dyes that may also be mentioned are the following dyes described in the Colour Index International 3rd edition:
  Disperse Red 17
  Acid Yellow 9
  Acid Black 1
  Basic Red 22
  Basic Red 76
  Basic Yellow 57
  Basic Brown 16
  Acid Yellow 36
  Acid Orange 7
  Acid Red 33
  Acid Red 35
  Basic Brown 17
  Acid Yellow 23
  Acid Orange 24
  Disperse Black 9.

Mention may also be made of 1-(4'-aminodiphenylazo)-2-methyl-4-[bis(β-hydroxyethyl)amino]benzene and 4-hydroxy-3-(2-methoxyphenylazo)-1-naphthalenesulfonic acid.

Among the quinone direct dyes that may be mentioned are the following dyes:
  Disperse Red 15
  Solvent Violet 13
  Acid Violet 43
  Disperse Violet 1
  Disperse Violet 4
  Disperse Blue 1
  Disperse Violet 8
  Disperse Blue 3
  Disperse Red 11
  Acid Blue 62
  Disperse Blue 7
  Basic Blue 22
  Disperse Violet 15
  Basic Blue 99
  and also the following compounds:
  1-N-methylmorpholiniumpropylamino-4-hydroxyanthraquinone
  1-aminopropylamino-4-methylaminoanthraquinone
  1-aminopropylaminoanthraquinone
  5-β-hydroxyethyl-1,4-diaminoanthraquinone
  2-aminoethylaminoanthraquinone
  1,4-bis(β,γ-dihydroxypropylamino)anthraquinone.

Among the azine dyes that may be mentioned are the following compounds:
  Basic Blue 17
  Basic Red 2.

Among the triarylmethane dyes that may be used according to the invention, mention may be made of the following compounds:
  Basic Green 1
  Acid Blue 9
  Basic Violet 3
  Basic Violet 14
  Basic Blue 7
  Acid Violet 49
  Basic Blue 26
  Acid Blue 7.

Among the indoamine dyes that may be used according to the invention, mention may be made of the following compounds:
  2-β-hydroxyethylamino-5-[bis(β-4'-hydroxyethyl)amino]anilino-1,4-benzoquinone;
  2-β-hydroxyethylamino-5-(2'-methoxy-4'-amino)anilino-1,4-benzoquinone;
  3-N(2'-chloro-4'-hydroxy)phenylacetylamino-6-methoxy-1,4-benzoquinoneimine;
  3-N(3'-chloro-4'-methylamino)phenylureido-6-methyl-1,4-benzoquinoneimine;
  3-[4'-N-(ethylcarbamylmethyl)amino]phenylureido-6-methyl-1,4-benzoquinoneimine.

Among the natural direct dyes that may be used according to the invention, mention may be made of lawsone, juglone, alizarin, purpurin, carminic acid, kermesic acid, purpurogallin, protocatechaldehyde, indigo, isatin, curcumin, spinulosin and apigenidin. Extracts or decoctions containing these natural dyes may also be used, and especially henna-based poultices or extracts.

The additional direct dye(s) preferably represent(s) from 0.001% to 20% by weight approximately, and even more preferably from 0.001% to 10% by weight approximately, relative to the total weight of the ready-to-use composition.

When the cosmetic adjuvant is an oxidation dye precursor, it is chosen from one or more oxidation bases and/or one or more couplers.

By way of example, the oxidation bases are chosen from phenylenediamines, bis(phenyl)alkylenediamines, para-aminophenols, ortho-aminophenols and heterocyclic bases other than the heterocyclic para-phenylenediamines of formula (I), and the addition salts thereof.

Among the para-phenylenediamines that may be mentioned, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylene-diamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid.

Among the para-phenylenediamines mentioned above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis-(β-hydroxyethyl)-para-phenylenediamine, 2-chloro-para-phenylenediamine and 2-β-acetylaminoethyloxy-para-phenylenediamine, and the addition salts thereof with an acid, are particularly preferred.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetra-methylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine and 1,8-bis(2,5-diaminophenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof.

Among the heterocyclic bases that may be mentioned, for example, are pyridine derivatives, pyrimidine derivatives and pyrazole derivatives.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine, and 3,4-diaminopyridine, and the addition salts thereof.

Other pyridine oxidation bases that are useful in the present invention are the 3-aminopyrazolo[1,5-a]pyridine oxidation bases or addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamino, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diamindpyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol and 3-aminopyrazolo[1,5-a]pyridin-7-ol, and the addition salts thereof.

Among the pyrimidine derivatives that may be mentioned are the compounds described, for example, in patents DE 2 359 399; JP 88-169 571; JP 05-63124; EP 0 770 375 or patent application WO 96/15765, for instance 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and the addition salts thereof, and the tautomeric forms thereof, when a tautomeric equilibrium exists.

Among the pyrazole derivatives that may be mentioned are the compounds described in patents DE 3 843 892 and DE 4 133 957, and patent applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof. 4,5-Diamino-1-(β-methoxyethyl)pyrazole may also be used.

The additional oxidation base(s) present in the composition of the invention is (are) generally present in an amount ranging from 0.001% to 20% by weight approximately, and preferably ranging from 0.005% to 6%, relative to the total weight of the dye composition.

If the composition according to the invention contains at least one oxidation base, it preferably contains one or more couplers conventionally used for dyeing keratin fibres. Among these couplers, mention may be made especially of meta-phenylenediamines, meta-aminophenols, meta-diphenols, naphthalene-based couplers and heterocyclic couplers, and also the addition salts thereof.

Examples that may be mentioned include 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene and 2,6-bis(β-hydroxyethylamino)toluene, and the addition salts thereof.

In the composition of the present invention, the coupler(s) is (are) generally present in an amount ranging from 0.001% to 20% and preferably ranging from 0.01% to 10% by weight approximately relative to the total weight of the dye composition.

In general, the addition salts of the oxidation bases and couplers that may be used in the context of the invention are chosen especially from the addition salts with an acid, such as the hydrochlorides, hydrobromides, sulfates, citrates, succinates, tartrates, lactates, tosylates, benzenesulfonates, phosphates and acetates, and the addition salts with a base, such as sodium hydroxide, potassium hydroxide, ammonia, amines or alkanolamines.

The oxidizing agents conventionally used for the oxidation dyeing of keratin fibres are, for example, hydrogen peroxide, urea peroxide, alkali metal bromates, persalts such as perborates and persulfates, peracids, and oxidase enzymes, among which mention may be made of peroxidases, 2-electron oxidoreductases such as uricases, and 4-electron oxygenases, for instance laccases. Hydrogen peroxide is particularly preferred.

The medium that is suitable for dyeing, also known as the dye support, is a cosmetic medium generally consisting of water or of a mixture of water and of at least one organic solvent to dissolve the compounds that are not sufficiently water-soluble. Examples of organic solvents that may be mentioned include $C_1$-$C_4$ lower alkanols such as ethanol and isopropanol; polyols and polyol ethers, for instance 2-butoxyethanol, propylene glycol, glycerol, polyol monoethers, propylene glycol monomethyl ether, diethylene glycol monoethyl ether and monomethyl ether, and also aromatic alcohols, for instance benzyl alcohol or phenoxyethanol, and mixtures thereof.

The solvents are preferably present in proportions preferably of between 1% and 40% by weight approximately and even more preferably between 5% and 30% by weight approximately relative to the total weight of the dye composition.

The pH of the dye composition in accordance with the invention is generally between 3 and 12 approximately, preferably between 5 and 11 approximately and even more particularly from 6 to 8.5. It may be adjusted to the desired value by means of acidifying or basifying agents usually used for dyeing keratin fibres, or alternatively using standard buffer systems.

Among the acidifying agents that may be mentioned, for example, are mineral or organic acids, for instance hydrochloric acid, orthophosphoric acid, sulfuric acid, carboxylic acids, for instance acetic acid, tartaric acid, citric acid or lactic acid, and sulfonic acids.

Among the basifying agents that may be mentioned, for example, are aqueous ammonia, alkaline carbonates, alkanolamines such as monoethanolamine, diethanolamine and triethanolamine and derivatives thereof, sodium hydroxide, potassium hydroxide and the compounds of formula (VI) below:

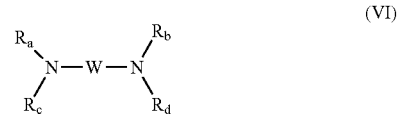

(VI)

in which W is a propylene residue optionally substituted with a hydroxyl group or a $C_1$-$C_4$ alkyl radical; $R_a$, $R_b$, $R_c$ and $R_d$, which may be identical or different, represent a hydrogen atom or a $C_1$-$C_4$ alkyl or $C_1$-$C_4$ hydroxyalkyl radical.

The dye composition according to the invention may be in various forms, such as in the form of liquids, creams or gels, or in any other form that is suitable for dyeing keratin fibres, and especially human hair.

The process of the present invention is a process in which the composition according to the present invention as defined above is applied to the fibres, the composition is left on the fibres for a period of between 5 minutes and 1 hour and preferably between 15 minutes and 1 hour, and the said fibres are then rinsed.

According to one particular embodiment, the composition of the invention free of oxidizing agent is applied to the keratin fibres in the presence of an oxidizing agent for a time sufficient to obtain the desired lightening. The oxidizing agent may be added to the composition of the invention just at the time of use, or it may be used starting with an oxidizing composition containing it, which is applied simultaneously with or sequentially to the composition of the invention.

According to one particular embodiment, the composition according to the present invention free of oxidizing agent comprises at least one oxidation dye precursor, and is mixed, preferably at the time of use, with a composition containing, in a medium that is suitable for dyeing, at least one oxidizing agent. The mixture obtained is then applied to the keratin fibres. After a leave-in time of from 5 minutes to 1 hour approximately and preferably 15 minutes to 1 hour approximately, the keratin fibres are rinsed, washed with shampoo, rinsed again and then dried.

The oxidizing composition may also contain various adjuvants conventionally used in hair dye compositions and as defined above.

The pH of the oxidizing composition containing the oxidizing agent is such that, after mixing with the dye composition, the pH of the resulting composition applied to the keratin fibres preferably ranges between 3 and 12 approximately, even more preferably between 5 and 11 and even more particularly between 6 and 8.5. It may be adjusted to the desired value by means of acidifying or basifying agents usually used in the dyeing of keratin fibres and as defined above.

The ready-to-use composition that is finally applied to the keratin fibres may be in various forms, such as in the form of liquids, creams or gels, or in any other form that is suitable for dyeing keratin fibres, and especially human hair.

A subject of the invention is also a multi-compartment device or dyeing "kit", in which a first compartment contains the dye composition according to the invention free of oxidizing agent and a second compartment contains an oxidizing agent. The compartment containing at least one dye of formula (I) may optionally contain at least one oxidation dye precursor defined above. This device may be equipped with a means for applying the desired mixture to the hair, such as the devices described in patent FR 2 586 913 in the name of the Applicant.

The examples that follow serve to illustrate the invention without, however, being limiting in nature.

EXAMPLES

Example 1

The composition according to the invention was prepared:

| Components | Amount |
| --- | --- |
| 3,7-Bis(bis(2-hydroxyethyl)amino)phenothiazin-5-ium bromide | 0.1 g |
| Ethanol | 5.0 g |
| Alkylpolyglucoside | 4.0 g AM |
| Preserving agent | qs |
| 2-Amino-2-methyl-1-propanol | qs pH 7.5 |
| Water | qs 100 |

This composition allows strong blue shades to be obtained on the hair.

Example 2

The composition according to the invention was prepared:

| Components | Amount |
| --- | --- |
| Internal salt of 3,6-bis[bis(2-hydroxyethyl)amino]-9-(2-carboxyphenyl)xanthylium | 0.1 g |
| Ethanol | 5.0 g |
| Alkylpolyglucoside | 4.0 g AM |
| Preserving agent | qs |
| 2-Amino-2-methyl-1-propanol | qs pH 7.5 |
| Water | qs 100 |

The composition allows bright fuchsia-pink shades to be obtained on the hair.

What is claimed is:

1. A cosmetic composition for dyeing keratin fibers comprising, in a suitable dyeing medium:

at least one hydroxyalkyl compound of formula (I) below:

$$\left[ R_3 \underset{R_4}{\overset{R_5}{\diagdown}} \underset{B}{\overset{A}{\bigodot}} \underset{R_6}{\overset{R_7}{\diagdown}} D \right] \overset{X}{\underset{R_2}{\diagdown}} N \diagdown z \qquad (I)$$

in which:
A is chosen from a nitrogen atom, a group $NR_9$, and a group $CR_9$;
B is chosen from oxygen, sulfur, and nitrogen atoms, and a group —$CR_9$;
A and B represent at least one hetero atom bearing a permanent cationic charge;
the electrical neutrality of the compound of formula (I) is ensured by an external counterion Y and/or by one of the substituents borne by the tricyclic nucleus;
D is chosen from amino groups, which are unsubstituted or mono- or disubstituted with at least one linear or branched $C_1$-$C_{24}$ alkyl group, which may be interrupted with at least one hetero atom and/or which may be substituted, the substituent(s) on the amino group together possibly forming a 5- to 12-membered optionally aromatic saturated or unsaturated heterocycle, these substituents themselves possibly being substituted with a sulfonic acid and/or a carboxylic acid; and amino groups which are mono- or disubstituted with an optionally substituted aryl group;
D being in the position para to the carbon that bears A or in the position para to the carbon that bears B;
the substituent —$N(zX)R_2$ is borne by the tricyclic nucleus;
z is chosen from linear or branched $C_1$-$C_{24}$ alkylene radicals, optionally interrupted with at least one hetero atom, bearing a substituent X of formula (II) below:

$$\underset{R_8'}{\overset{R_8}{\diagdown}} \!\!\!\diagup \!\! [OR_1]_n \qquad (II)$$

$R_1$ is chosen from hydrogen and $C_1$-$C_{24}$ hydroxyalkyl groups;
$R_8$ and $R_8'$ are chosen, independently of each other, from hydrogen and $C_1$-$C_{24}$ alkyl groups which may be interrupted with at least one group chosen from hetero atoms and carbonyl groups and/or which may be substituted;
n ranges from 1 to 20;
$R_2$ is chosen from hydrogen; linear or branched $C_1$-$C_{24}$ alkyl radicals, which may be interrupted with at least one group chosen from hetero atoms and carbonyl groups and/or which may be substituted; and hydroxyalkyl groups;
$R_3$, $R_4$, $R_5$, $R_6$ and $R_7$ are chosen, independently of each other, from hydrogen, halogen atoms; linear or branched $C_1$-$C_{24}$ alkyl radicals, which may be interrupted with at least one group chosen from hetero atoms and carbonyl groups and/or which may be substituted; amino groups, which are unsubstituted or mono- or disubstituted with at least one linear or branched $C_1$-$C_{24}$ alkyl group, which may be interrupted with at least one group chosen from hetero atoms and carbonyl groups and/or which may be substituted, the substituent(s) on the amino group together possibly forming a 5- to 12-membered optionally aromatic saturated or unsaturated heterocycle; optionally substituted with a carboxylic acid and/or a sulfonic acid;

when $R_2$ is hydrogen, then D, $R_3$, $R_4$, $R_5$, $R_6$ or $R_7$ is a disubstituted amino group;

$R_9$ is chosen from linear or branched, substituted or unsubstituted $C_1$-$C_{24}$ alkyl groups, benzyl and aryl radicals optionally substituted with at least one group chosen from $C_1$-$C_{24}$ alkyl groups, $C_1$-$C_{24}$ alkoxy groups, carboxylic acid groups, and/or sulfonic acid groups;

and the mesomeric forms thereof; and at least one cosmetic adjuvant.

2. The composition of claim 1, wherein the at least one hydroxyalkyl compound is of formula (III):

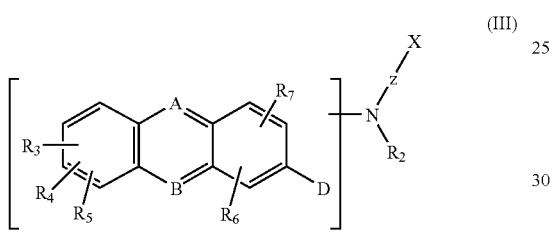

(III)

in which:

A is chosen from a nitrogen atom, a group $NR_9$, and a group $CR_9$;

B is chosen from oxygen, sulfur, and nitrogen atoms, and —$CR_9$;

A and B represent at least one hetero atom bearing a permanent cationic charge;

the electrical neutrality of the compound of formula (I) is ensured by an external counterion Y and/or by one of the substituents borne by the tricyclic nucleus;

D is chosen from amino groups, which are unsubstituted or mono- or disubstituted with at least one linear or branched $C_1$-$C_{24}$ alkyl group, which may be interrupted with at least one hetero atom and/or which may be substituted, the substituent(s) on the amino group together possibly forming a 5- to 12-membered optionally aromatic saturated or unsaturated heterocycle, these substituents themselves possibly being substituted with a sulfonic acid and/or a carboxylic acid; and amino groups which are mono- or disubstituted with an optionally substituted aryl group; the substituent —N(zX)$R_2$ is borne by the tricyclic nucleus;

z is chosen from linear or branched $C_1$-$C_{24}$ alkylene radicals, optionally interrupted with at least one hetero atom, bearing a substituent X of formula (II) below:

(II)

$R_1$ is chosen from hydrogen and a $C_1$-$C_{24}$ hydroxyalkyl group;

$R_8$ and $R_8'$ are chosen, independently of each other, from hydrogen and $C_1$-$C_{24}$ alkyl groups which may be interrupted with at least one group chosen from hetero atoms and carbonyl groups and/or which may be substituted;

$R_2$ is chosen from hydrogen; linear or branched $C_1$-$C_{24}$ alkyl radicals, which may be interrupted with at least one group chosen from hetero atoms and carbonyl groups and/or which may be substituted; and hydroxyalkyl groups;

$R_3$, $R_4$, $R_5$, $R_6$ and $R_7$ are chosen, independently of each other, from hydrogen, halogen atoms; linear or branched $C_1$-$C_{24}$ alkyl radicals, which may be interrupted with at least one group chosen from hetero atoms and carbonyl groups and/or which may be substituted; amino groups, which are unsubstituted or mono- or disubstituted with at least one linear or branched $C_1$-$C_{24}$ alkyl group, which may be interrupted with at least one group chosen from hetero atoms and carbonyl groups and/or which may be substituted, the substituent(s) on the amino group together possibly forming a 5- to 12-membered optionally aromatic saturated or unsaturated heterocycle; optionally substituted with a carboxylic acid and/or a sulfonic acid;

when $R_2$ is hydrogen, then D, $R_3$, $R_4$, $R_5$, $R_6$ or $R_7$ is a disubstituted amino group;

$R_9$ is chosen from linear or branched, substituted or unsubstituted $C_1$-$C_{24}$ alkyl groups, benzyl and aryl radicals optionally substituted with at least one group chosen from $C_1$-$C_{24}$ alkyl groups, $C_1$-$C_{24}$ alkoxy groups, carboxylic acid groups, and/or sulfonic acid groups;

and the mesomeric forms thereof.

3. The composition of claim 2, wherein the compound of formula (III) is chosen from:

internal salt of 3,6-bis[bis(2-hydroxyethyl)amino]-9-(2-sulfophenyl)xanthylium;

sodium salt of 3-[bis(2-hydroxyethyl)amino]-6-[(2-bromophenyl)amino]-9-(2,4-disulfophenyl)xanthylium;

sodium salt of 3-[bis(2-hydroxyethyl)amino]-9-(2,4-disulfophenyl)-6-[(2-fluorophenyl)amino]xanthylium;

sodium salt of 3-[bis(2-hydroxyethyl)amino]-6-[(2-methoxy-5-sulfophenyl)amino]-9-(2-sulfophenyl)xanthylium;

sodium salt of 3-[bis(2-hydroxyethyl)amino]-9-(2,4-disulfophenyl)-6-[[2-(1-methylethoxy)phenyl]amino]xanthylium;

poly(oxy-1,2-ethanediyl), α-hydro-ω-hydroxy ether with the internal salt of 3,6-[bis(2-hydroxyethyl)amino]-9-(2-carboxyphenyl)xanthylium;

internal salt of 3,6-bis[bis(2-hydroxyethyl)amino]-9-(2-carboxyphenyl) xanthylium;

3,7-bis(bis(2-hydroxyethyl)amino)phenothiazin-5-ium bromide;

3-[bis(2-hydroxyethyl)amino]-7-(diethylamino)phenoxazin-5-ium; and

3-[bis(2-hydroxyethyl)amino]-7-(dimethylamino)phenoxazin-5-ium.

4. The composition of claim 1, wherein the compound is of formula (IV):

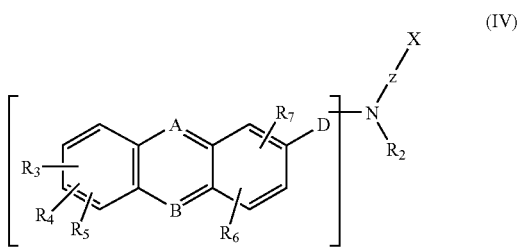

(IV)

in which:

A is chosen from nitrogen, a group NR$_9$, and a group CR$_9$;

B is chosen from oxygen, sulfur, and nitrogen atoms, and a group —CR$_9$;

A and B representing at least one hetero atom bearing a permanent cationic charge;

the electrical neutrality of the compound of formula (I) is ensured by an external counterion Y and/or by one of the substituents borne by the tricyclic nucleus;

D is chosen from amino groups, which are unsubstituted or mono- or disubstituted with at least one linear or branched C$_1$-C$_{24}$ alkyl group, which may be interrupted with at least one hetero atom and/or which may be substituted, the substituent(s) on the amino group together possibly forming a 5- to 12-membered optionally aromatic saturated or unsaturated heterocycle, these substituents themselves possibly being substituted with a sulfonic acid and/or a carboxylic acid; and amino groups which are mono- or disubstituted with an optionally substituted aryl group;

the substituent —N(zX)R$_2$ is borne by the tricyclic nucleus;

z is chosen from linear or branched C$_1$-C$_{24}$ alkylene radicals, optionally interrupted with at least one hetero atom, bearing a substituent X of formula (II) below:

(II)

R$_1$ is chosen from hydrogen and C$_1$-C$_{24}$ hydroxyalkyl groups;

R$_8$ and R$_8$' are chosen, independently of each other, from hydrogen and C$_1$-C$_{24}$ alkyl groups which may be interrupted with at least one group chosen from hetero atoms and carbonyl groups and/or which may be substituted;

n ranges from 1 to 20;

R$_2$ is chosen from hydrogen; linear or branched C$_1$-C$_{24}$ alkyl radicals, which may be interrupted with at least one group chosen from hetero atoms and carbonyl groups and/or which may be substituted; and hydroxyalkyl groups;

R$_3$, R$_4$, R$_5$, R$_6$ and R$_7$ are chosen, independently of each other, from hydrogen, halogen atoms; linear or branched C$_1$-C$_{24}$ alkyl radicals, which may be interrupted with at least one group chosen from hetero atoms and carbonyl groups and/or which may be substituted; amino groups, which are unsubstituted or mono- or disubstituted with at least one linear or branched C$_1$-C$_{24}$ alkyl group, which may be interrupted with at least one group chosen from hetero atoms and carbonyl groups and/or which may be substituted, the substituent(s) on the amino group together possibly forming a 5-to 12-membered optionally aromatic saturated or unsaturated heterocycle; optionally substituted with a carboxylic acid and/or a sulfonic acid;

when R$_2$ is hydrogen, then D, R$_3$, R$_4$, R$_5$, R$_6$ or R$_7$ is a disubstituted amino group;

R$_9$ is chosen from linear or branched, substituted or unsubstituted C$_1$-C$_{24}$ alkyl groups, benzyl and aryl radicals optionally substituted with at least one group chosen from C$_1$-C$_{24}$ alkyl groups, C$_1$-C$_{24}$ alkoxy groups, carboxylic acid groups, and/or sulfonic acid groups;

and the mesomeric forms thereof.

5. The composition of claim 4, wherein the compound of formula (IV) is chosen from:
   3-amino-7-[bis(2-hydroxyethyl)amino]-5-phenylphenazinium chloride,
   3-[bis(2-hydroxyethyl)amino]-7-(dimethylamino)-5-(4-methoxy-phenyl)phenazinium iodide;
   3-amino-7-[(2-hydroxyethyl)methylamino]-5-phenylphenazinium chloride;
   3-amino-7-[(2,3-dihydroxypropyl)(2-hydroxyethyl)amino]-5-phenyl-phenazinium chloride;
   3-(dimethylamino)-7-[(2-hydroxyethyl)methylamino]-5-(4-methoxy-phenyl)phenazinium iodide;
   3-[bis(2-cyanoethyl)amino]-7-[(2-hydroxyethyl)methylamino]-5-(4-methoxyphenyl)phenazinium iodide; and
   3-[bis(2-cyanoethyl)amino]-7-[bis(2-hydroxyethyl)amino]-5-(4-methoxyphenyl)phenazinium iodide.

6. The composition of claim 1, wherein the at least one hydroxyalkyl compound is present in an amount ranging from 0.001% to 20% by weight relative to the total weight of the composition.

7. The composition of claim 6, wherein the at least one hydroxyalkyl compound is present in an amount ranging from 0.1% to 5% by weight relative to the total weight of the composition.

8. The composition of claim 1, wherein the at least one cosmetic adjuvant is chosen from surfactants, polymers, ceramides and pseudoceramides, vitamins and provitamins, sunscreens, solid compounds, direct dyes other than those of formula (I), oxidation dye precursors, sequestering agents, plasticizers, solubilizers, acidifying agents, basifying agents, neutralizers, mineral and organic thickeners, antioxidants, hydroxy acids, solvents, penetrating agents, buffers, dispersants, conditioning agents and preserving agents.

9. The composition of claim 1, further comprising at least one additional direct dye.

10. The composition of claim 1, further comprising at least one oxidation dye precursor chosen from oxidation bases and couplers.

11. The composition of claim 10, wherein the composition comprises at least one oxidation base chosen from paraphenylenediamines, bis(phenyl)alkylenediamines, para-aminophenols, ortho-aminophenols and heterocyclic bases, and the addition salts thereof.

12. The composition of claim 11, wherein the at least one oxidation base is present in an amount ranging from 0.001% to 20% by weight relative to the total weight of the composition.

13. The composition of claim 12, wherein the at least one oxidation base is present in an amount ranging from 0.005% to 6% by weight relative to the total weight of the composition.

14. The composition of claim 10, further comprising at least one coupler chosen from meta-phenylenediamines, meta-aminophenols, meta-diphenols, naphthalene-based couplers and heterocyclic couplers, and the addition salts thereof.

15. The composition of claim 14, wherein the at least one coupler is chosen from 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene and 2,6-bis(β-hydroxyethylamino)toluene, and the addition salts thereof.

16. The composition of claim 14, wherein the at least one coupler is present in an amount ranging from 0.001% to 20% by weight relative to the total weight of the composition.

17. The composition of claim 16, wherein the at least one coupler is present in an amount ranging from 0.01% to 10% by weight relative to the total weight of the composition.

18. The composition of claim 1, further comprising at least one hydroxylated solvent chosen from ethanol, propylene glycol, glycerol and polyol monoethers.

19. The composition of claim 1, further comprising at least one oxidizing agent chosen from hydrogen peroxide, urea peroxide, alkali metal bromates, persalts, peracids and oxidase enzymes.

20. A process for dyeing keratin fibers, comprising
applying a cosmetic composition to the keratin fibers,
leaving the composition on the fibers for a period ranging from 5 minutes to 1 hour, and
rinsing the fibers;
wherein the cosmetic composition comprises, in a suitable dyeing medium:
at least one hydroxyalkyl compound of formula (I) below:

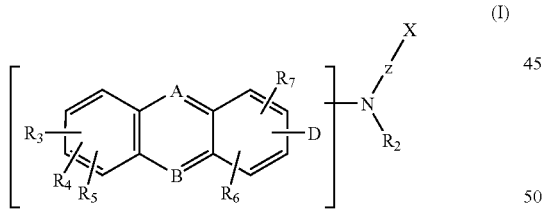

in which:
A is chosen from nitrogen, a $NR_9$ group, and a $CR_9$ group;
B is chosen from oxygen, sulfur, and nitrogen atoms, and a —$CR_9$ group:
A and B representing at least one hetero atom bearing a permanent cationic charge;
the electrical neutrality of the compound of formula (I) is ensured by an external counterion Y and/or by one of the substituents borne by the tricyclic nucleus;
D is chosen from amino groups, which are unsubstituted or mono- or disubstituted with at least one linear or branched $C_1$-$C_{24}$ alkyl group, which may be interrupted with at least one hetero atom and/or which may be substituted, the substituent(s) on the amino group together possibly forming a 5- to 12-membered optionally aromatic saturated or unsaturated heterocycle, these substituents themselves possibly being substituted with a sulfonic acid and/or a carboxylic acid; and amino groups which are mono- or disubstituted with an optionally substituted aryl group;
D being in the position para to the carbon that bears A or in the position para to the carbon that bears B;
the substituent —$N(zX)R_2$ is borne by the tricyclic nucleus;
z is chosen from linear or branched $C_1$-$C_{24}$ alkylene radicals, optionally interrupted with at least one hetero atom, bearing a substituent X of formula (II) below:

$R_1$ is chosen from hydrogen and $C_1$-$C_{24}$ hydroxyalkyl groups;
$R_8$ and $R_8'$ are chosen, independently of each other, from hydrogen and $C_1$-$C_{24}$ alkyl groups which may be interrupted with at least one group chosen from hetero atoms and carbonyl groups and/or which may be substituted;
n ranges from 1 to 20;
$R_2$ is chosen from hydrogen; linear or branched $C_1$-$C_{24}$ alkyl radicals, which may be interrupted with at least one group chosen from hetero atoms and carbonyl groups and/or which may be substituted; and hydroxyalkyl groups;
$R_3$, $R_4$, $R_5$, $R_6$ and $R_7$ are chosen, independently of each other, from hydrogen, halogen atoms; linear or branched $C_1$-$C_{24}$ alkyl radicals, which may be interrupted with at least one group chosen from hetero atoms and carbonyl groups and/or which may be substituted; and amino groups, which are unsubstituted or mono- or disubstituted with at least one linear or branched $C_1$-$C_{24}$ alkyl group, which may be interrupted with at least one group chosen from hetero atoms and carbonyl groups and/or which may be substituted, the substituent(s) on the amino group together possibly forming a 5- to 12-membered optionally aromatic saturated or unsaturated heterocycle; optionally substituted with a carboxylic acid and/or a sulfonic acid;
when $R_2$ is hydrogen, then D, $R_3$, $R_4$, $R_5$, $R_6$ or $R_7$ is a disubstituted amino group;
$R_9$ is chosen from linear or branched, substituted or unsubstituted $C_1$-$C_{24}$ alkyl groups, benzyl and aryl radicals optionally substituted with at least one group chosen from $C_1$-$C_{24}$ alkyl groups, $C_1$-$C_{24}$ alkoxy groups, carboxylic acid groups, and/or sulfonic acid groups;
and the mesomeric forms thereof; and
at least one cosmetic adjuvant.

21. A process for lightening keratin fibers, comprising
applying a cosmetic composition free of oxidizing agent to the keratin fibers,
applying an oxidizing composition to the keratin fibers simultaneously with or sequentially to the dye composition,
leaving the compositions on the fibers for a period ranging from 5 minutes to 1 hour, then rinsing the fibers, washing the fibers with shampoo, rinsing again and drying the fibers;
wherein the cosmetic composition comprises, in a suitable dyeing medium:
at least one hydroxyalkyl compound of formula (I) below:

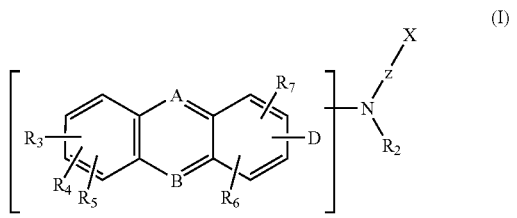

in which:
A is chosen from nitrogen, a group $NR_9$, and a group $CR_9$;
B is chosen from oxygen, sulfur, and nitrogen atoms, and a group $—CR_9$;
A and B representing at least one hetero atom bearing a permanent cationic charge;
the electrical neutrality of the compound of formula (I) is ensured by an external counterion Y and/or by one of the substituents borne by the tricyclic nucleus;
D is chosen from amino groups, which are unsubstituted or mono- or disubstituted with at least one linear or branched $C_1$-$C_{24}$ alkyl group, which may be interrupted with at least one hetero atom and/or which may be substituted, the substituent(s) on the amino group together possibly forming a 5- to 12-membered optionally aromatic saturated or unsaturated heterocycle, these substituents themselves possibly being substituted with a sulfonic acid and/or a carboxylic acid; and amino groups which are mono- or disubstituted with an optionally substituted aryl group;
D being in the position para to the carbon that bears A or in the position para to the carbon that bears B;
the substituent $—N(zX)R_2$ is borne by the tricyclic nucleus;
z is chosen from linear or branched $C_1$-$C_{24}$ alkylene radicals, optionally interrupted with at least one hetero atom, bearing a substituent X of formula (II) below:

$R_1$ is chosen from hydrogen and $C_1$-$C_{24}$ hydroxyalkyl groups;
$R_8$ and $R_8'$ are chosen, independently of each other, from hydrogen and $C_1$-$C_{24}$ alkyl groups which may be interrupted with at least one group chosen from hetero atoms and carbonyl groups and/or which may be substituted;
n ranges from 1 to 20;
$R_2$ is chosen from hydrogen; linear or branched $C_1$-$C_{24}$ alkyl radicals, which may be interrupted with at least one group chosen from hetero atoms and carbonyl groups and/or which may be substituted; and hydroxyalkyl groups;
$R_3$, $R_4$, $R_5$, $R_6$ and $R_7$ are chosen, independently of each other, from hydrogen, halogen atoms; linear or branched $C_1$-$C_{24}$ alkyl radicals, which may be interrupted with at least one group chosen from hetero atoms and carbonyl groups and/or which may be substituted; and amino groups, which are unsubstituted or mono- or disubstituted with at least one linear or branched $C_1$-$C_{24}$ alkyl group, which may be interrupted with at least one group chosen from hetero atoms and carbonyl groups and/or which may be substituted, the substituent(s) on the amino group together possibly forming a 5- to 12-membered optionally aromatic saturated or unsaturated heterocycle; optionally substituted with a carboxylic acid and/or a sulfonic acid;
when $R_2$ is hydrogen, then D, $R_3$, $R_4$, $R_5$, $R_6$ or $R_7$ is a disubstituted amino group;
$R_9$ is chosen from linear or branched, substituted or unsubstituted $C_1$-$C_{24}$ alkyl groups, benzyl and aryl radicals optionally substituted with at least one group chosen from $C_1$-$C_{24}$ alkyl groups, $C_1$-$C_{24}$ alkoxy groups, carboxylic acid groups, and/or sulfonic acid groups;
and the mesomeric forms thereof; and
at least one cosmetic adjuvant.

22. A process for dyeing keratin fibers, comprising
applying a cosmetic composition comprising at least one oxidation dye precursor and free of oxidizing agent to the keratin fibers,
applying an oxidizing composition simultaneously with or sequentially to the dye composition,
leaving the compositions on the fibers for a period ranging from 5 minutes to 1 hour, and
then rinsing the fibers, washing the fibers with shampoo, rinsing the fibers again and drying said fibers;
wherein the cosmetic composition comprises, in a suitable dyeing medium:
at least one hydroxyalkyl compound of formula (I) below:

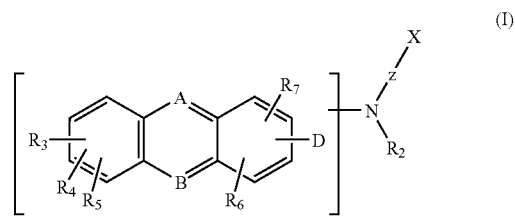

in which:
A is chosen from nitrogen, a group $NR_9$, and a group $CR_9$;
B is chosen from oxygen, sulfur, and nitrogen atoms, and a group $—CR_9$;
A and B representing at least one hetero atom bearing a permanent cationic charge;
the electrical neutrality of the compound of formula (I) is ensured by an external counterion Y and/or by one of the substituents borne by the tricyclic nucleus;
D is chosen from amino groups, which are unsubstituted or mono- or disubstituted with at least one linear or branched $C_1$-$C_{24}$ alkyl group, which may be interrupted with at least one hetero atom and/or which may be substituted, the substituent(s) on the amino group together possibly forming a 5- to 12-membered optionally aromatic saturated or unsaturated heterocycle, these substituents themselves possibly being substituted with a sulfonic acid and/or a carboxylic acid; and amino groups which are mono- or disubstituted with an optionally substituted aryl group;

D being in the position para to the carbon that bears A or in the position para to the carbon that bears B;

the substituent —N(zX)R$_2$ is borne by the tricyclic nucleus;

z is chosen from linear or branched C$_1$-C$_{24}$ alkylene radicals, optionally interrupted with at least one hetero atom, bearing a substituent X of formula (II) below:

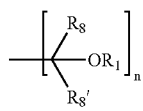

R$_1$ is chosen from hydrogen and C$_1$-C$_{24}$ hydroxyalkyl groups;

R$_8$ and R$_8$' are chosen, independently of each other, from hydrogen and C$_1$-C$_{24}$ alkyl groups which may be interrupted with at least one group chosen from hetero atoms and carbonyl groups and/or which may be substituted;

n ranges from 1 to 20;

R$_2$ is chosen from hydrogen; linear or branched C$_1$-C$_{24}$ alkyl radicals, which may be interrupted with at least one group chosen from hetero atoms and carbonyl groups and/or which may be substituted; and hydroxyalkyl groups;

R$_3$, R$_4$, R$_5$, R$_6$ and R$_7$ are chosen, independently of each other, from hydrogen, halogen atoms; linear or branched C$_1$-C$_{24}$ alkyl radicals, which may be interrupted with at least one group chosen from hetero atoms and carbonyl groups and/or which may be substituted; and amino groups, which are unsubstituted or mono- or disubstituted with at least one linear or branched C$_1$-C$_{24}$ alkyl group, which may be interrupted with at least one group chosen from hetero atoms and carbonyl groups and/or which may be substituted, the substituent(s) on the amino group together possibly forming a 5- to 12-membered optionally aromatic saturated or unsaturated heterocycle; optionally substituted with a carboxylic acid and/or a sulfonic acid;

when R$_2$ is hydrogen, then D, R$_3$, R$_4$, R$_5$, R$_6$ or R$_7$ is a disubstituted amino group;

R$_9$ is chosen from linear or branched, substituted or unsubstituted C$_1$-C$_{24}$ alkyl groups, benzyl and aryl radicals optionally substituted with at least one group chosen from C$_1$-C$_{24}$ alkyl groups, C$_1$-C$_{24}$ alkoxy groups, carboxylic acid groups, and/or sulfonic acid groups;

and the mesomeric forms thereof; and at least one cosmetic adjuvant.

23. A multi-compartment device comprising a first compartment containing a cosmetic composition free of oxidizing agent;

wherein the cosmetic composition comprises, in a suitable dyeing medium:

at least one hydroxyalkyl compound of formula (I) below:

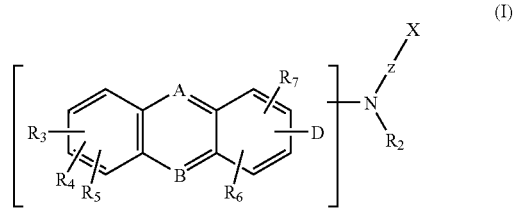

in which:

A is chosen from nitrogen, a group NR$_9$, and a group CR$_9$;

B is chosen from oxygen, sulfur, and nitrogen atoms, and a group —CR$_9$;

A and B representing at least one hetero atom bearing a permanent cationic charge;

the electrical neutrality of the compound of formula (I) is ensured by an external counterion Y and/or by one of the substituents borne by the tricyclic nucleus;

D is chosen from amino groups, which are unsubstituted or mono- or disubstituted with at least one linear or branched C$_1$-C$_{24}$ alkyl group, which may be interrupted with at least one hetero atom and/or which may be substituted, the substituent(s) on the amino group together possibly forming a 5- to 12-membered optionally aromatic saturated or unsaturated heterocycle, these substituents themselves possibly being substituted with a sulfonic acid and/or a carboxylic acid; and amino groups which are mono- or disubstituted with an optionally substituted aryl group;

D being in the position para to the carbon that bears A or in the position para to the carbon that bears B;

the substituent —N(zX)R$_2$ is borne by the tricyclic nucleus;

z is chosen from linear or branched C$_1$-C$_{24}$ alkylene radicals, optionally interrupted with at least one hetero atom, bearing a substituent X of formula (II) below:

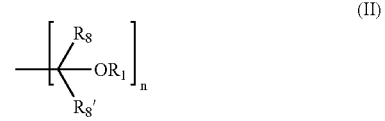

R$_1$ is chosen from hydrogen and C$_1$-C$_{24}$ hydroxyalkyl groups;

R$_8$ and R$_8$' are chosen, independently of each other, from hydrogen and C$_1$-C$_{24}$ alkyl groups which may be interrupted with at least one group chosen from hetero atoms and carbonyl groups and/or which may be substituted;

n ranges from 1 to 20;

R$_2$ is chosen from hydrogen; linear or branched C$_1$-C$_{24}$ alkyl radicals, which may be interrupted with at least one group chosen from hetero atoms and carbonyl groups and/or which may be substituted; and hydroxyalkyl groups;

R$_3$, R$_4$, R$_5$, R$_6$ and R$_7$ are chosen, independently of each other, from hydrogen, halogen atoms; linear or branched C$_1$-C$_{24}$ alkyl radicals, which may be interrupted with at least one group chosen from hetero atoms and carbonyl groups and/or which may be substituted; and amino groups, which are unsubstituted or mono- or disubstituted with at least one linear or branched $C_1$-$C_{24}$ alkyl group, which may be interrupted with at least one group chosen from hetero atoms and carbonyl groups and/or which may be substituted, the substituent(s) on the amino group together possibly forming a 5- to 12-membered optionally aromatic saturated or unsaturated heterocycle; optionally substituted with a carboxylic acid and/or a sulfonic acid;

when $R_2$ is hydrogen, then D, $R_3$, $R_4$, $R_5$, $R_6$ or $R_7$ is a disubstituted amino group;

$R_9$ is chosen from linear or branched, substituted or unsubstituted $C_1$-$C_{24}$ alkyl groups, benzyl and aryl radicals optionally substituted with at least one group chosen from $C_1$-$C_{24}$ alkyl groups, $C_1$-$C_{24}$ alkoxy groups, carboxylic acid groups, and/or sulfonic acid groups;

and the mesomeric forms thereof; and at least one cosmetic adjuvant; and a second compartment containing a composition comprising an oxidizing agent, when the cosmetic adjuvant contained in the dye composition is other than an oxidizing agent.

24. The device according to claim 23, wherein the first compartment comprises an oxidation dye precursor, when the cosmetic adjuvant contained in the dye composition is other than an oxidation dye precursor.

* * * * *

UNITED STATES PATENT AND TRADEMARK OFFICE
CERTIFICATE OF CORRECTION

PATENT NO. : 7,326,258 B2 Page 1 of 1
APPLICATION NO. : 11/155501
DATED : February 5, 2008
INVENTOR(S) : Alain Lagrange It is certified that error appears in the above-identified patent and that said Letters Patent is hereby corrected as shown below:

In claim 4, column 24, line 4, "5-to" should read --5- to--.

In claim 20, column 25, line 54, "nitrogen,a" should read --nitrogen, a--.

In claim 20, column 25, line 56, "group:" should read --group;--.

Signed and Sealed this

Eighth Day of July, 2008

JON W. DUDAS
*Director of the United States Patent and Trademark Office*